(12) United States Patent
Sofranko

(10) Patent No.: US 11,021,420 B1
(45) Date of Patent: Jun. 1, 2021

(54) OXYGEN TRANSFER AGENT CONDITIONING SYSTEMS AND METHODS

(71) Applicant: Bio2Electric, LLC, Woburn, MA (US)

(72) Inventor: John A. Sofranko, Weston, MA (US)

(73) Assignee: Bio2Electric, LLC, Woburn, MA (US)

(*) Notice: Subject to any disclaimer, the term of this patent is extended or adjusted under 35 U.S.C. 154(b) by 0 days.

(21) Appl. No.: 16/863,678

(22) Filed: Apr. 30, 2020

Related U.S. Application Data

(60) Provisional application No. 62/843,509, filed on May 5, 2019, provisional application No. 62/849,851, filed
(Continued)

(51) Int. Cl.
| | |
|---|---|
| *C07C 5/48* | (2006.01) |
| *B01J 37/20* | (2006.01) |
| *C07C 2/82* | (2006.01) |
| *B01J 37/12* | (2006.01) |
| *B01J 37/18* | (2006.01) |
| *B01J 27/187* | (2006.01) |

(Continued)

(52) U.S. Cl.
CPC .............. *C07C 5/48* (2013.01); *B01J 27/055* (2013.01); *B01J 27/187* (2013.01); *B01J 35/0026* (2013.01); *B01J 37/12* (2013.01); *B01J 37/18* (2013.01)

(58) Field of Classification Search
None
See application file for complete search history.

(56) References Cited

U.S. PATENT DOCUMENTS

| | | | |
|---|---|---|---|
| 2,126,817 A * | 8/1938 | Rosen .................. | C07C 5/46 585/330 |
| 3,526,478 A * | 9/1970 | Pelczarski ............. | C01B 3/348 423/650 |

(Continued)

FOREIGN PATENT DOCUMENTS

| | | |
|---|---|---|
| WO | 2015168601 A2 | 11/2015 |
| WO | 2018232133 A1 | 12/2018 |

OTHER PUBLICATIONS

Neal et al., Oxidative Dehydrogenation of Ethane: A Chemical Looping Approach, Energy Technolgy, 2016, vol. 4, pp. 1-10.
(Continued)

*Primary Examiner* — Philip Y Louie
(74) *Attorney, Agent, or Firm* — RatnerPrestia

(57) ABSTRACT

Improvements in the commercial viability of oxygen transfer agents (OTAs) and/or catalysts associated with the OCM and the ODH of hydrocarbons to olefins through enhancement of one or more of the selectivity, yield, rate and lifetime of the OTA and/or catalyst is described by one or more of (i) exposing the OTA or the catalyst to a sulfur-containing compound at a site or at a time that is different from where and when the saturated hydrocarbon is converted by the OTA or the catalyst to an unsaturated hydrocarbon; (ii) increasing the particle density of the OTA or the catalyst by treating the OTA or the catalyst with a reducing agent at a site different from where the saturated hydrocarbon is converted by the OTA or by the catalyst to an unsaturated hydrocarbon; and (iii) removing non-selective redox oxygen (NSRO) present on the OTA by subjecting the OTA to a gas that is substantially free of any molecular oxygen.

30 Claims, 8 Drawing Sheets

Related U.S. Application Data on May 18, 2019, provisional application No. 62/850,399, filed on May 20, 2019.

(51) Int. Cl.
    *B01J 35/00*      (2006.01)
    *B01J 27/055*      (2006.01)

(56) References Cited

U.S. PATENT DOCUMENTS

| | | | |
|---|---|---|---|
| 3,666,687 A * | 5/1972 | Croce | B01J 37/20 502/220 |
| 3,793,392 A * | 2/1974 | Martin | B01J 27/043 585/661 |
| 4,477,313 A | 10/1984 | Andersson | |
| 4,497,971 A * | 2/1985 | Eastman | B01J 23/76 502/210 |
| 4,499,322 A | 2/1985 | Jones et al. | |
| 4,670,619 A | 6/1987 | Withers, Jr. et al. | |
| 4,751,336 A * | 6/1988 | Jezl | C07C 2/84 585/322 |
| 4,788,372 A | 11/1988 | Gaffney | |
| 4,795,842 A | 1/1989 | Gaffney et al. | |
| 4,795,849 A | 1/1989 | Gaffney et al. | |
| 4,879,427 A | 11/1989 | Sofranko | |
| 6,518,476 B1 * | 2/2003 | Culp | C07C 2/84 585/655 |
| 10,138,182 B2 | 11/2018 | Sofranko et al. | |
| 2004/0140245 A1 * | 7/2004 | Ramani | C07C 5/48 208/48 R |
| 2017/0313637 A1 * | 11/2017 | Sofranko | B01J 27/285 |
| 2018/0185806 A1 | 7/2018 | Sofranko | |

OTHER PUBLICATIONS

De Vries et al., "The Thermal Decomposition of Potassium and Sodium-Pyrosulfate" J. Inorg. Nucl. Chem., 1969, vol. 31, pp. 1307-1313.

Sofranko et al., "The Oxidative Conversion of Methane to Higher Hydrocarbons", Journal of Catalysis, 1987, vol. 103, pp. 302-310.

* cited by examiner

OXYGEN TRANSFER AGENT CONDITIONING SYSTEMS AND METHODS

CROSS REFERENCE TO RELATED APPLICATIONS

This application claims the benefit of and priority from U.S. Provisional Application Nos. 62/850,399, filed on May 20, 2019; 62/849,851, filed May 18, 2019; and 62/843,509, filed May 5, 2019 the disclosures of each of which is incorporated by reference herein in its entirety for all purposes.

TECHNICAL FIELD

The present disclosure relates to methods for conditioning a catalyst and/or oxygen transfer agent used in the oxidative coupling of methane (OCM) and/or in the oxidative dehydrogenation (ODH) of ethane and higher hydrocarbons to improve reaction yields and/or selectivities and/or resistance of the catalyst and/or oxygen transfer agent to attrition and/or to extend the operating lifetime of the reactors in which the OCM and the ODH reactions are run.

BACKGROUND OF THE INVENTION

Ethylene and propylene are important building blocks for the petrochemical industry and are used in manufacturing polymers such as polyethylene, polypropylene, polystyrene and additional chemical compounds of commercial interest. Over 90% of the global olefin production originates from the high temperature steam cracking of naphtha or ethane and propane. The steam cracking process, which utilizes furnaces, is highly energy intensive, and 1.5 to 2 tons of carbon dioxide are produced for every ton of olefin product.

Natural gas production from shale deposits has dramatically increased supply in recent years. As a result of the continued global demand for olefins and the potential for a new growing supply of ethane and propane available in natural gas liquids from shale deposits, a significant amount of interest and investment is currently directed to expanding the capacity of ethylene and propylene derived from these new sources. Numerous olefin grass root and expansion projects are either under contract or in the planning stages to take advantage of the relatively low cost liquids from wet shale gas. However, there are several environmental and cost challenges to operating at this level of new capacity.

Olefin production is the largest emitter of $CO_2$ and NOx in the organic chemical industry. With worldwide ethylene production at approximately 150 MT/yr, the industry emits 150-300 MT/yr of $CO_2$ and roughly 1.4 MT/yr of NOx. Projects located in severe EPA non-attainment zones are challenged by the increased cost of NOx control. The total greenhouse gas (GHG) emission profile, reported in $CO_2$ equivalents, is another critical part of the permitting process for all production expansions.

The industry continues to push for a production technology that: (1) generates higher overall yields of ethylene and propylene; (2) increases the run length time between furnace turnarounds (e.g., inspections, repairs, improvements, etc.); (3) lowers steam and energy utilization; and (4) lowers all GHGs, including carbon dioxide and NOx. The ODH of ethane and propane to ethylene and propylene, respectively, offers a potential solution for addressing these needs, such as a production route that can significantly reduce $CO_2$ emissions and virtually eliminate NOx emissions from world scale plants.

The ODH of ethane is a selective catalytic process that produces primarily ethylene and water as products and is an exothermic reaction (reaction 1).

$$CH_3CH_3 + \tfrac{1}{2}O_2 \rightarrow CH_2CH_2 + H_2O \; \Delta H_0 = -105 \text{ kJ/mol} \quad (1)$$

The per pass yield of the ODH reaction is not limited by thermodynamic equilibrium, as it is in pyrolysis (reaction 2).

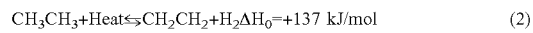
$$CH_3CH_3 + \text{Heat} \leftrightarrows CH_2CH_2 + H_2 \; \Delta H_0 = +137 \text{ kJ/mol} \quad (2)$$

ODH provides an opportunity to improve the efficiency of olefin production. While a significant amount of research has been done over the last 25 years, most reported ODH processes are not cost-effective because they involve highly exothermic catalytic reactions with co-fed oxygen and platinum group metal catalysts. Thus, there is a significant need for improved materials for facilitating ODH, as well as reactors and processes that incorporate these improved materials.

The Oxidative Coupling of Methane (OCM) and the Oxidative Dehydrogenation (ODH) of ethane and higher hydrocarbons to olefinic products represent reactions of substantial commercial value. These conversions may be accomplished (I) catalytically, by reacting a hydrocarbon and an oxygen-containing gas in the presence of a catalyst, or by (I) a redox oxygen transfer mode whereby a hydrocarbon is reacted with an Oxygen Transfer Agent (OTA) which supplies the oxygen needed for the formation of water. Either system is exemplified by the following reaction (reaction 3).

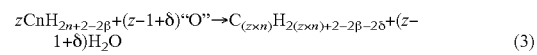
$$zC_nH_{2n+2-2\beta} + (z-1+\delta)\text{"O"} \rightarrow C_{(z \times n)}H_{2(z \times n)+2-2\beta-2\delta} + (z-1+\delta)H_2O \quad (3)$$

where z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation. The oxygen "O" may be supplied by the reduction of a metal oxide transfer agent or via molecular oxygen in the presence of a suitable catalyst. The agent that supplies the oxygen, whether a reducible metal oxide or another type of catalyst or catalyst system may be referred to as an oxygen transfer agent (OTA).

The present invention addresses the need for improved yields and selectivities and rates for both the oxidative coupling of methane and the oxidative dehydrogenation of ethane and higher saturated hydrocarbons by conditioning of the catalyst and/or OTA as described herein.

SUMMARY OF THE INVENTION

An aspect of the invention is a process for enhancing at least one of, or at least two of, or all three of, the selectivity, rate and yield associated with using an oxygen transfer agent or a catalyst for oxidative dehydrogenation of a saturated hydrocarbon to an unsaturated hydrocarbon, the process comprising:

treating the oxygen transfer agent or the catalyst with a sulfur-containing compound at a site or at a time that is different from where or when the saturated hydrocarbon is converted by the treated oxygen transfer agent or catalyst to the unsaturated hydrocarbon, and reacting the treated oxygen transfer agent or catalyst with the saturated hydrocarbon to produce the unsaturated hydrocarbon.

Another aspect of the invention is a process for reducing corrosion of reactor components in a reactor where a saturated hydrocarbon is converted by an oxygen transfer agent or a catalyst to an unsaturated hydrocarbon, the process comprising:

treating the oxygen transfer agent or catalyst at a site that is different from the reactor with a sulfur-containing compound that enhances at least one of, or at least two of, or at least three of, the selectivity, rate and yield associated with using the oxygen transfer agent or catalyst, and reacting the treated oxygen transfer agent or catalyst with the saturated hydrocarbon in the reactor to produce the unsaturated hydrocarbon.

Another aspect of the invention is a process for increasing the particle density of the oxygen transfer agent or catalyst to enhance the attrition resistance of the particles by treating the oxygen transfer agent or catalyst with a reducing agent at a site different from where the saturated hydrocarbon is converted by the oxygen transfer agent or catalyst to the unsaturated hydrocarbon.

Yet another aspect of the invention is a process for increasing the selectivity of an oxygen transfer agent for oxidative dehydrogenation of a saturated hydrocarbon by removing non-selective redox oxygen (NSRO) present on the oxygen transfer agent by subjecting the oxygen transfer agent to a gas that is non-oxidizing, such as a gas that is substantially free of any molecular oxygen.

BRIEF DESCRIPTION OF THE DRAWINGS

The drawings are intended to illustrate specific embodiments of the invention and are not intended to otherwise limit the scope of the invention as described.

FIG. 4 illustrates the beneficial effects of $SO_3$ after it was injected into the nitrogen purge stream which include Increased ethane conversion and higher olefin yields.

DETAILED DESCRIPTION

Figure 1:
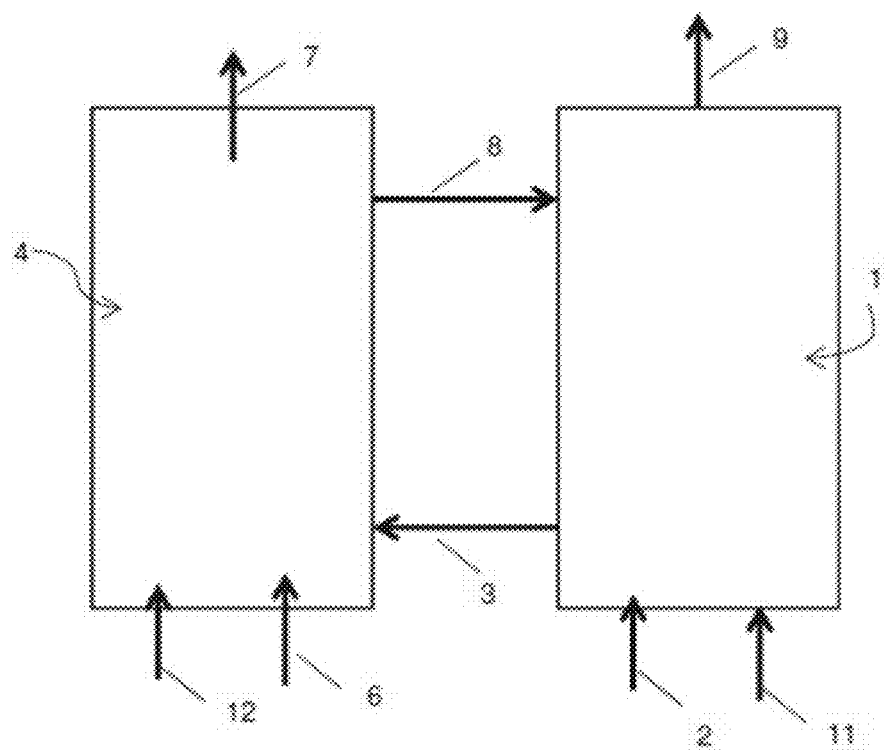
FIG. 1 shows a generalized conventional reactor system for implementing both OCM and ODH of ethane and higher hydrocarbons using redox cyclic mode or chemical looping techniques. In an exemplary embodiment of this system, a sulfur-containing gas is introduced directly into the hydrocarbon conversion reactor 1 via inlet 11 where it acts to promote and/or stabilize the OCM or ODH reaction while the hydrocarbon is introduced via inlet 2 and the olefin product exits via outlet 9. In the regeneration vessel 4, the reacted OTA in reduced form enters via inlet 3, is regenerated upon exposure to oxygen, and is then reintroduced back into the reactor 1 via inlet 8.

An objective of the present invention is to increase the commercial viability of oxygen transfer agents (OTAs) used for the ODH of hydrocarbons and for OTAs and catalysts used for OCM. To qualify as a commercially viable OTA or catalyst, the material should exhibit at least the following attributes: (a) ability to promote a high rate of conversion of a hydrocarbon feedstock to the desired olefin product(s); (b) ability to provide high selectivities and yields in generating the desired olefin products; and (c) maintain the attributes of (a) and (b) over hundreds, and preferably, thousands of reaction (e.g., redox) cycles. Many effective conventional catalysts and OTAs used for the production of olefins via the OCM or ODH reaction contain alkali and alkaline earth metals as promoters. These promoters modify the active metal oxide materials to enhance the formation of the desired olefin products and to minimize less desired products such as carbon dioxide, carbon monoxide and coke. See, e.g., U.S. Pat. Nos. 4,499,322; and 4,477,313. However, these promoters can be stripped away from the catalysts under the OCM and ODH reaction conditions which generally involves operation temperatures of greater than 700° C. Alkali replenishment has been suggested as a method to compensate for this alkali loss. See, e.g., U.S. Pat. No. 4,795,842. Steam is a product of the OCM and ODH reactions and may be added to the reactor feed to enhance olefin product selectivity. See, e.g., U.S. Pat. No. 4,788,372.

To Increase the commercial viability of OTAs and/or catalysts associated with the OCM or the ODH of hydrocarbons to olefins, the inventor observed that the following actions, either alone or in various combinations, unexpectedly enhanced one or more of, such as two or more of, such as three or more of, such as all four of, the selectivity, yield, rate and lifetime of the OTA and/or catalyst: (i) exposing (or treating or contacting) the oxygen transfer agent or the catalyst to a sulfur-containing compound for the purpose of altering one or more of the physical or chemical properties of the OTA or catalyst to achieve a desired enhancement (i.e., "conditioning" of the OTA or catalyst) at a site or at a time that is different from where and when the saturated hydrocarbon starting material is converted by the oxygen transfer agent or the catalyst to the unsaturated hydrocarbon product; (i) Increasing the particle density of the oxygen transfer agent or the catalyst by exposing (or treating or contacting) the oxygen transfer agent or the catalyst with a reducing agent at a site different from where the saturated hydrocarbon starting material is converted by the oxygen transfer agent or by the catalyst to the unsaturated hydrocarbon product; and (ill) removing non-selective redox oxygen (NSRO) present on the surface of oxygen transfer agent by subjecting the oxygen transfer agent to a gas that is substantially free of any molecular oxygen. Each of these methodologies is described in more detail below.

Exposure of the Catalyst or OTA to a Sulfur-Containing Compound

The inventor discovered that sulfur-containing compounds, typically in gas form, can be used to modify and enhance the activities and selectivities of OCM and ODH catalysts and OTAs by exposing the catalysts and OTAs to the sulfur-containing compound (for the purpose of conditioning the catalysts and OTAs) when the catalysts and OTAs are not in contact with the hydrocarbon feed in the reactor where the OCM or ODH reaction occurs. These beneficial effects associated with the introduction of the sulfur-containing compound at a location other than in the actual reaction vessel(s) or at a time other than when the OCM or ODH reaction is occurring has not been reported. Instead, conventional techniques introduce the sulfur-containing compound in the reactor(s) where the saturated hydrocarbon starting material is converted by an oxygen transfer agent or a catalyst to the unsaturated hydrocarbon product at the time the OCM or ODH reaction is taking place. See, e.g., U.S. Pat. Nos. 4,670,619; 4,879,427; WO 2015/168601; and U.S. 20180185806. The observation of the beneficial effects achieved by treating catalysts and OTAs with sulfur-containing compounds outside of the environment of the reactor allows for more options when constructing reactor systems for OCM and/or for the ODH of hydrocarbons that alleviate possible problems of design and function, such as the corrosion of reactor components caused by introduction of a sulfur-containing gas. The conditioning of the catalyst and/or the OTA by the sulfur-containing compound may also be accomplished under more desirable reaction conditions than those currently employed by necessity in the hydrocarbon conversion reactor, thus allowing for substantially more flexibility for successfully implementing the catalyst and/or OTA conditioning on an industrial scale in a variety of industrial designs.

FIG. 1 shows a general conventional reactor system for the redox cyclic mode or chemical looping method for implementing OCM and ODH. Vessel 1 is the reactor. Hydrocarbon gas is fed into the reactor via 2 and the desired olefin products, along with the less desired $CO_x$, hydrogen and water, exit the reactor via 9. In this system, the OTA becomes reduced by providing oxygen for the OCM and ODH reactions. The reduced OTA is then transported to the regenerator vessel 4 via the transfer line 3. Vessels 1 and 4 are typically fluidized beds, but may also be denser phase particle moving bed reactors.

Alternatively, the circulating fluid bed system may be replaced by fixed bed or fluid bed reactors whereby necessary feeds are switched via a valve system. In an exemplary embodiment of the present invention, an oxygen-containing gas such as $O_2$ or air is introduced to vessel 4 via 6, which re-oxidizes the OTA and supplies it with the necessary oxygen to participate in the ODH of hydrocarbons. The regenerated OTA is transported back to the reactor 1 via transfer line 8 and the depleted oxygen-containing waste gas, and any $CO_x$ products that may have resulted from coke combustion, exit via 7.

It has been previously reported that sulfur-containing gases have been introduced to the reactor vessel 1 via 11 for the purpose of achieving a promoting or stabilizing effect within the reactor during hydrocarbon conversion. In an embodiment of the present invention, a sulfur-containing compound (in gas form) is introduced to the reactor vessel 4 via 12 which is outside of reactor vessel 4. The resulting increase that was observed in the rate of the ODH reaction by taking this approach in addition to the noted improvements in both product selectivity and yield were unexpected.

Figure 2:
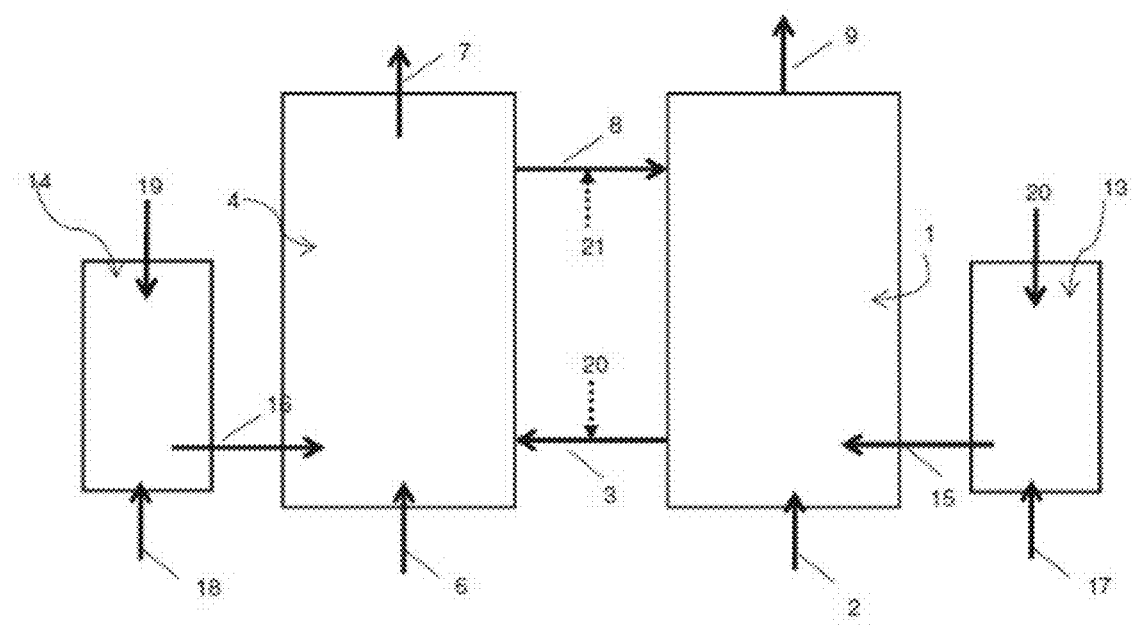
FIG. 2 shows a conventional reactor system that has been modified compared to the system in FIG. 1 to benefit from the various aspects of the present invention. In one embodiment, the catalyst or the OTA for the OCM or ODH reaction is pretreated with a sulfur-containing gas in the catalyst treatment vessel 20 before being introduced into the hydrocarbon conversion reactor 1. In another embodiment, a sulfur-containing gas is introduced along with oxygen into the regeneration vessel 4 to recondition the reacted (reduced) OTA or catalyst. In yet another embodiment, a sulfur-containing gas is introduced into the conditioning vessel 14 (as an alternative to being introduced into the catalyst treatment vessel 13) where the catalyst or OTA is conditioned before entry into the regeneration vessel 4. In another embodiment, a sulfur-containing gas is introduced in both the conditioning vessel 14 and the catalyst treatment vessel 20. One or more of the additional methodologies of densification of the OTA or catalyst and removal of NSRO from the OTA can also be employed for further improvements in the yield, rate and/or selectivity associated with the OTA or catalyst.

FIG. 2 shows additional exemplary embodiments of the present invention. The depicted reactor system for OCM or ODH is similar to that of FIG. 1 with the exception that introduction of the benefit-conferring sulfur-containing compound(s) to improve and condition the catalyst and/or OTA is performed outside of reaction vessel 1 and regenerator vessel 4. In an exemplary embodiment, the sulfur-containing compound (in gas form) is introduced via 17 to a catalyst treatment vessel 13 along with the continuous addition of the unconditioned catalyst or OTA via 20. Once sufficiently conditioned by the sulfur-containing gas, the catalyst or OTA could be fed into the reactor vessel 1 (where the ODH or OCM reaction takes place) at a rate suitable to maintain the desired conversion and yields of the ODH or OCM reaction. In other exemplary embodiments of the present invention, another conditioning vessel 14 could be employed in addition to, or as a substitute for, the catalyst treatment vessel 13. In another exemplary embodiment, the conditioning sulfur-containing compound (in gas form) is introduced via 18 into conditioning vessel 14 along with the un-conditioned catalyst and/or OTA via 19. Once sufficiently conditioned by the sulfur-containing gas in vessel 14, the conditioned catalyst is introduced to the regeneration vessel 4 via 16, where the rate of addition of the conditioned catalyst is sufficient to maintain the desired rate and selectivities to the desired OCM and ODH olefin products. In other exemplary embodiments, vessels 13 and 14 represent standpipes or gas stripper sections in the circulation bed reactors, and 17 and 18 are for sulfur-containing purge gases.

In an exemplary embodiment of the present invention, the conditioning of the catalyst or OTA with a sulfur-containing compound (typically in gas form) occurs separately from the reactor system and, as such, may take place at a different location on the OCM or ODH production site or at a remotely located catalyst or OTA manufacturing site. In these instances, the post-conditioned catalyst could be introduced via 20 or 21 (see the hashed arrows) as depicted in FIG. 2. Again, the rate of introduction of the conditioned catalyst or OTA would be sufficient to maintain the desired rate and selectivity to the ODH and/or OCM olefin products.

In other exemplary embodiments, one or more of the components of the catalyst or OTA is treated with a sulfur-containing compound either during or before the manufacturing process. In another exemplary embodiment, the catalyst or OTA raw materials (such as magnesium or manganese oxides) are treated with a sulfur-containing compound before the catalyst or OTA is manufactured. In an exemplary embodiment, a sulfur-containing reagent is employed at the catalyst manufacturing site. In a particular embodiment, sulfuric acid (as a sulfur-containing compound) is used to treat magnesia, which is a common starting material for OCM and OTA compounds.

Increasing the Particle Density of the Catalyst or OTA

Densifcation of a catalyst or OTA by exposure to a reducing agent has been observed to significantly improve the fluid bed attrition resistance of the catalyst particles or OTA particles, which in turn results in a longer operating lifetime of the catalyst or OTA. This commercially valuable process has been reported for OCM OTAs (see, e.g., U.S. Pat. No. 4,795,849) but not its integration into an ethane (or higher hydrocarbons) ODH reactor system. In view of the fact that ethane pyrolyzes to produce hydrogen gas and hydrogen gas serves as an effective reducing agent for increasing the densification of a catalyst or OTA, the "in situ" generation of hydrogen gas in an ethane (or higher hydrocarbon) ODH reactor system provides a facile and cost-effective opportunity for improving the attrition resistance of the catalyst or OTA particles that are present.

In FIG. 1, the OTA is reduced by providing oxygen for the OCM and ODH reactions. The reduced OTA is then transported to the regenerator vessel 4 via the transfer line 3. In an exemplary embodiment, reactor vessel 1 and regeneration vessel 4 are fluidized beds. In another exemplary embodiment, vessels 1 and 4 are denser phase particle moving bed reactors. Alternatively, this circulating fluid bed system may be replaced by fixed bed or fluid bed reactors whereby necessary feeds are switched via a valve system. In an exemplary embodiment of the present invention, an oxygen-containing gas such as air is introduced to 4 via 6 thereby re-oxidizing the OTA for its use in a hydrocarbon ODH reaction. For commercial application, it Imperative that the catalyst or OTA has a high attrition resistance. Since it appears that high attrition resistance correlates well with high particle density, it is desirable to increase the particle density of the OTAs to at least that of standard fluid catalytic cracking (FCC) catalysts (about 1 g/cc) or higher. In addition, increasing the density of the OTA allows for higher oxygen transport rates and also improved heat transfer between vessels 1 and 4 of FIG. 1.

While hydrogen gas is an effective reducing reagent, it is desirable to employ a method that does not require the feeding of a flammable gas to the calcination system. As a result, an exemplary embodiment of the present invention is the use of n situ gasification of carbonaceous materials for the formation of reducing gases, such as hydrogen and carbon monoxide.

Therefore, at temperatures above 350° C. the following is a general reaction for the in situ generation of a reducing gas (reaction 4)

$$C_nH_y + H_2O + Heat \rightarrow H_2 + CO \quad (4)$$

Suitable carbonaceous materials ($C_nH_y$) include, but are not limited to, carbon, coal, biomass, hydrocarbons that lay down coke on the catalyst, waste plastics or any carbonaceous material capable of forming a reducing gas with steam and in the presence of the catalyst or OTA.

FIG. 2 shows additional embodiments of the present invention. The reactor system depicted in FIG. 2 for ODH is similar to that of FIG. 1, but with the added possibility of introducing reducing (densifcation) gases or gasification materials into vessels 13 and/or 14 along with the catalyst and/or OTA. This process may be accomplished by batch-wise addition or by continuous feeding of sufficiently densified OTA to the reactor system in order to maintain the appropriate level of catalyst charge to the system catalyst that is sufficient to maintain the desired rates and selectivities of the targeted OCM and ODH olefinic products. In exemplary embodiments, vessels 13 and/or 14 act as standpipes or as gas stripper sections while densification with the reducing gas or gasification takes place.

An aspect of the present invention is the use of reducing gas densifcation methods as described herein to not only increase the density of the OCM or ODH catalyst or OTA but also to modify the physical properties of any molten material that might be present on the surface of the catalyst or OTA. The high temperature fluidization characteristics of materials described in, for example, WO2018/232133 should benefit by the methods described herein. In this example, the molten material would become less "sticky" and thereby improve the OTA's ability to fluidize and flow at reaction conditions.

In an exemplary embodiment, the OCM and ODH systems described herein involve catalysts or OTAs used in a redox cyclic mode, but the catalyst and OTA conditioning techniques as described herein may also be applied to improve the stability and olefinic product yields for catalytic OCM and ODH which are run by co-feeding a hydrocarbon and an oxygen-containing gas to a reactor.

Removal of Non-Selective Redox Oxygen (NSRO) Present on the Oxygen Transfer Agent In an attempt to increase the commercial viability of OTAs used for the ODH of hydrocarbons and for OCM by obtaining the highest possible selectivities to generate the desired olefin products and to minimize the formation of undesirable carbon oxides ($CO_x$) and coke, it was observed that the oxidation state of the OTA was optimized by subjecting the OTA to a non-oxidizing purge gas. By employing this technique, molecular oxygen that is loosely bound to the OTA is removed from the OTA before reaction of the OTA in an ODH reaction. Since the loosely bound oxygen unexpectedly appears to render the OTA less selective for the desired dehydrogenation and more selective for undesired $CO_x$ formation, this inexpensive and "low-tech" step of removing or diminishing loosely bound oxygen from an OTA has the potential to result in significant savings when employed on an industrial scale.

In general, the method of increasing the selectivity of the OTA to desired olefinic products by treatment of the OTA with a non-oxidizing gas applies to any case where the oxygen in reaction 1 is supplied by a metal oxide comprising the OTA, whereby only the most selective oxygen of equation 5 is used in the reaction 3.

$$MO^{oxidized} \leftrightarrows MO^{reduced} + \text{"O"} \quad (5)$$

A simplified example of the equilibrium of metal oxides is shown in equation 6 where manganese oxide is representative of any metal oxide (see, e.g., Kemmitt, Comprehensive Inorganic Chem. 5, 802 (1973)). Over a range in temperature from 600° C. to approximately 1,500° C., and at one atmosphere of air, manganese is in equilibrium with its more reduced forms as the environmental temperature increases. In general, the more oxidized forms of manganese, and other metal oxides, are less selective for promoting reaction 3 than the more reduced forms. Therefore, an objective of the present invention is to tune the level and oxidation state of the OTA to achieve the most selective OCM or ODH performance by removal of Non-Selective Redox Oxygen (NSRO) and thereby maintain viable hydrocarbon conversion rates.

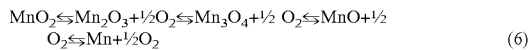

$$MnO_2 \leftrightarrows Mn_2O_3 + \tfrac{1}{2}O_2 \leftrightarrows Mn_3O_4 + \tfrac{1}{2}O_2 \leftrightarrows MnO + \tfrac{1}{2}O_2 \leftrightarrows Mn + \tfrac{1}{2}O_2 \qquad (6)$$

Equation 6 is for illustrative purposes only and the present invention is not limited to oxides of manganese or to simple oxides of any metal. Instead, the present invention pertains to any OTA whereby the level and type of metal oxide can be synchronized to provide a more selective form of the OTA by purging or stripping of NSRO with any gas that is non-oxidizing or substantially free of any molecular oxygen or fuel such that it can remove the NSRO from the OTA and also partially reduce the OTA. The invention is not constrained by the mechanism of the oxygen transfer promoting reaction 3, as it could occur via direct interaction of the hydrocarbons with the OTA surface, or via a gas phase reaction of $O_2$ released from the OTA, or any combination thereof. The reduced metal oxide of equation 5 can be re-oxidized by any oxygen-containing gas such as air or other oxygen-containing gas such as oxides of sulfur and nitrogen. Higher selectivities to the desired olefinic products are obtained if NSRO is first removed from the metal oxide before it comes in contact with the target hydrocarbon feed. In this way, only the more selective oxygen is donated from the OTA in order to promote reaction 3.

The above described methods for conditioning of the catalysts and OTAs may be applied individually or in any combination thereof in order to provide a catalyst or OTA for use in the OCM or ODH system that yields commercially viable reaction rates and desired product yields.

Oxygen Transfer Agent

A useful catalyst or oxygen transfer agent (OTA) will not only promote high conversion of the hydrocarbon feeds to high selectivities of the desired products, thereby minimizing unwanted $CO_x$ and coke products, but the catalyst or oxygen transfer agent desirably has certain physical properties in order to be successfully used in ODH and OCM reactors. These desirable physical properties include: an ability to maintain fluidization at reaction temperatures; good physical strength and low attrition under fluidization conditions and able to maintain these properties over many redox (or chemical looping) cycles; an ability to maintain the desired reaction conversion rate and selectivity to the desired products for at least one month; an absence of high toxicity; suitability for use in in a circulating fluid bed reactor.

While the composition of the OTA or catalyst as described herein, especially for its use in the OCM or the ODH of hydrocarbons, is not particularly limited, exemplary OTA compositions are comprised of one or more of Mg, Mn, Fe, Mo, TI, V, Pr, Cu and La and are promoted by one or more of alkali metals, alkaline earth metals, boron, sulfur, tungstic acid salts, halide salts or any material that imparts beneficial characteristics to the OTA, where the OTA particles can be densified by conventional means or as otherwise described herein.

Depending on how it is prepared, the OTA may contain varying levels of sulfur-containing compounds. In an exemplary embodiment, the OTA contains 0.001 wt % to 0.5 wt % of sulfur, such as 0.003 to 0.4 wt %, such as 0.004 to 0.4 wt %, such as 0.005 to 0.3 wt %, such as 0.007 to 0.2 wt %. If insufficient sulfur is present in the composition of materials used to prepare the OTA, a treatment to increase the sulfur to a level in excess of 0.001 wt % or other desirable levels can be performed.

Methods for Carrying Out the OCM and ODH Reactions:

Methods for carrying out the OCM reaction and ODH of saturated hydrocarbons are well documented in the art (see, e.g., U.S. Pat. No. 10,138,182; Neil et al., Energy Technology 4: 1200-1208 (2016); Sofranko et al., Journal of Catalysis 302-310 (1987)). The methodologies described herein for conditioning the OTA and/or catalyst used in the OCM or ODH reactions of saturated hydrocarbons are robust and can be used in combination with almost any OCM or ODH process.

Hydrocarbon Feed:

As defined herein, a saturated hydrocarbon that is suitable for oxidative dehydrogenation may be branched, cyclic or contain one or more unsaturated carbon-carbon bonds (i.e., —C=C— and/or —C≡C). An exemplary embodiment of such a compound is 1-butene ($CH_2$=$CH_2$—$CH_2$—$CH_3$) which contains an ODH-reactive saturated portion (—$CH_2$—$CH_3$) of the molecule as well as an unsaturated portion ($CH_2$=CH—). Suitable ODH hydrocarbon feeds for use in embodiments of the present invention may be selected from ethane; propane; isomers of butane; Isomers of butene, Isomers of pentane; Isomers of pentene; isomers of hexane; cyclohexane; Isomers of hexene; cycohexene; and mixtures thereof.

Aspects of the Invention

Various aspects of the invention may be summarized as follows:

Aspect 1: A process for enhancing at least one of selectivity, rate and yield associated with using an oxygen transfer agent or a catalyst for oxidative dehydrogenation of a saturated hydrocarbon, the process comprising:

treating the oxygen transfer agent or the catalyst with a sulfur-containing compound at a site or at a time that is different from where and when the saturated hydrocarbon is converted by the treated oxygen transfer agent or the catalyst to an unsaturated hydrocarbon, and then reacting the treated oxygen transfer agent or the catalyst with the saturated hydrocarbon to produce the unsaturated hydrocarbon.

Aspect 2: The process of Aspect 1, wherein the site where the oxygen transfer agent or the catalyst is treated with a sulfur-containing compound is a catalyst treatment vessel.

Aspect 3: The process of Aspect 1 or 2, wherein the site where the oxygen transfer agent or the catalyst is treated with a sulfur-containing compound is a conditioning vessel where unconditioned oxygen transfer agent or catalyst is conditioned.

Aspect 4: The process of any Aspects 1 to 3, wherein the site where the oxygen transfer agent or the catalyst is treated with a sulfur-containing compound is a catalyst treatment vessel and a conditioning vessel where unconditioned oxygen transfer agent or catalyst is conditioned.

Aspect 5: The process of any of Aspects 1 to 4, wherein the site where the oxygen transfer agent or the catalyst is treated with a sulfur-containing compound is a standpipe or a gas stripper section in a circulation bed reactor.

Aspect 6: The process of any of Aspects 1 to 5, wherein the site where the oxygen transfer agent or the catalyst is treated with a sulfur-containing compound is a location at a facility where the unsaturated hydrocarbon is produced.

Aspect 7: The process of any of Aspects 1 to 6, wherein the site where the oxygen transfer agent or the catalyst is treated with a sulfur-containing compound is a location where the catalyst is manufactured.

Aspect 8: The process of Aspect 1, wherein the oxygen transfer agent or the catalyst is treated with a sulfur-containing compound at a time that is before the saturated hydrocarbon is converted by the treated oxygen transfer agent or the catalyst to an unsaturated hydrocarbon.

Aspect 9: The process of Aspect 1, wherein the oxygen transfer agent or the catalyst is treated with a sulfur-containing compound at a time that is after the saturated hydrocarbon is converted by the treated oxygen transfer agent or the catalyst to an unsaturated hydrocarbon.

Aspect 10: The process of any of Aspects 1 to 9, wherein the sulfur-containing compound is a solid, liquid or a gas.

Aspect 11: The process of any of Aspects 1 to 10, wherein the sulfur-containing compound is selected from the group consisting of dimethyl sulfide, diethyl sulfide, ethylene sulfide, diamyl sulfide, diallyl sulfide, dicyclohexyl sulfide, $SO_3$, $SO_2$, $H_2S$ and $CS_2$.

Aspect 12: The process of any of Aspects 1 to 11, wherein the saturated hydrocarbon is a $C_2$-$C_6$ saturated hydrocarbon.

Aspect 13: The process of any of Aspects 1 to 12, wherein the saturated hydrocarbon is ethane or propane.

Aspect 14: The process of any of Aspects 1 to 11, wherein the saturated hydrocarbon is ethane, where the ethane is generated by oxidative coupling of methane.

Aspect 15: A process of any of Aspects 1 to 14 for reducing corrosion of reactor components in a reactor where a saturated hydrocarbon is converted by an oxygen transfer agent or a catalyst to an unsaturated hydrocarbon, the process comprising:

treating the oxygen transfer agent or the catalyst at a site that is different from the reactor with a sulfur-containing compound that enhances at least one of selectivity, rate and yield associated with using the oxygen transfer agent or the catalyst, and reacting the treated oxygen transfer agent or the catalyst with the saturated hydrocarbon to produce the unsaturated hydrocarbon.

Aspect 16: A process for increasing particle density of an oxygen transfer agent or a catalyst for use in an oxidative dehydrogenation of a saturated hydrocarbon to enhance attrition resistance of the particles by treating the oxygen transfer agent or the catalyst with a reducing agent at a site different from where the saturated hydrocarbon is converted by the oxygen transfer agent or the catalyst to the unsaturated hydrocarbon, where the site is any of those recited in Aspects 1-7.

Aspect 17: The process of Aspect 16, wherein treatment of the oxygen transfer agent or the catalyst with the reducing agent occurs before the process of any of Aspects 1-15.

Aspect 18: The process of Aspect 16, wherein treatment of the oxygen transfer agent or the catalyst with the reducing agent occurs after the process of any of Aspects 1-15.

Aspect 19. The process of Aspect 16, wherein treatment of the oxygen transfer agent or the catalyst with the reducing agent occurs at approximately the same time as the process of any of Aspects 1-15.

Aspect 20: The process of any of Aspects 16 to 19, wherein the reducing agent is hydrogen gas, nitrous oxide or carbon monoxide.

Aspect 21: The process of any of Aspects 16 to 20, wherein the hydrogen gas and carbon monoxide are generated in situ.

Aspect 22: The process of any of Aspects 16 to 21, wherein the hydrogen gas and/or the carbon monoxide are by-products formed from the oxidative dehydrogenation of the saturated hydrocarbon to the unsaturated hydrocarbon.

Aspect 23: The process of any of Aspects 16 to 22, wherein the reducing agent is generated from combustion of carbonaceous materials.

Aspect 24: The process of any of Aspects 16 to 23, wherein the particle density is increased by at least 10%.

Aspect 25: The process of any of Aspects 16 to 24, wherein the particle density is increased by at least 20%.

Aspect 26: The process of any of Aspects 16 to 25, wherein the particle density is increased by at least 30%.

Aspect 27: A process for increasing the selectivity of an oxygen transfer agent for oxidative dehydrogenation of a saturated hydrocarbon by removing non-selective redox oxygen (NSRO) present on the oxygen transfer agent by subjecting the oxygen transfer agent to a gas that does not oxidize the oxygen transfer agent.

Aspect 28. The process of Aspect 27, wherein subjecting the oxygen transfer agent to the non-oxidizing gas occurs before the process of any of Aspects 1 to 15 and before the process of any of Aspects 16 to 26.

Aspect 29. The process of Aspect 27, wherein subjecting the oxygen transfer agent to the non-oxidizing gas occurs after the process of any of Aspects 1 to 15 and after the process of any of Aspects 16 to 26.

Aspect 30. The process of Aspect 27, wherein subjecting the oxygen transfer agent to the non-oxidizing gas occurs before the process of any of Aspects 1 to 15 but after the process of any of Aspects 16 to 26.

Aspect 31. The process of Aspect 27, wherein subjecting the oxygen transfer agent to the non-oxidizing gas occurs after the process of any of Aspects 1 to 15 but before the process of any of Aspects 16 to 26.

Aspect 32. The process of Aspect 27, wherein subjecting the oxygen transfer agent to the non-oxidizing gas occurs at approximately the same time as the process of any of Aspects 1 to 15 but before the process of any of Aspects 16 to 26.

Aspect 33. The process of Aspect 27, wherein subjecting the oxygen transfer agent to the non-oxidizing gas occurs at approximately the same time as the process of any of Aspects 1 to 15 but after the process of any of Aspects 16 to 26.

Aspect 34. The process of Aspect 27, wherein subjecting the oxygen transfer agent to the non-oxidizing gas occurs before the process of any of Aspects 1 to 15 but at approximately the same time as the process of any of Aspects 16 to 26.

Aspect 35. The process of Aspect 27, wherein subjecting the oxygen transfer agent to the non-oxidizing gas occurs after the process of any of Aspects 1 to 15 but at approximately the same time as the process of any of Aspects 16 to 26.

Aspect 36. The process of Aspect 27, wherein subjecting the oxygen transfer agent to the non-oxidizing gas occurs at approximately the same time as the process of any of Aspects 1 to 15 and at approximately the same time as the process of any of Aspects 16 to 26.

Aspect 37. The process of any of Aspects 27 to 36, wherein the gas is substantially free of any molecular oxygen.

Aspect 38: The process of any of Aspects 27 to 37, wherein subjecting the oxygen transfer agent to the gas partially reduces the oxygen transfer agent.

Aspect 39: The process of any of Aspects 27 to 38, wherein the gas is nitrogen gas, argon, methane, oxides of carbon, oxides of nitrogen or oxides of sulfur.

Aspect 40: The process of any of Aspects 27 to 39, wherein selectivity is increased by at least 5%.

Aspect 40: The process of any of Aspects 27 to 40, wherein the selectivity is increased by at least 10%.

Aspect 41: The process of any of Aspects 27 to 41, wherein the selectivity is increased by at least 20%.

EXAMPLES

The following non-limiting examples are provided for the purpose of elucidating the advantages obtained from aspects of the present invention and are not intended to limit the invention to only these exemplary embodiments.

Example 1

Figure 3:
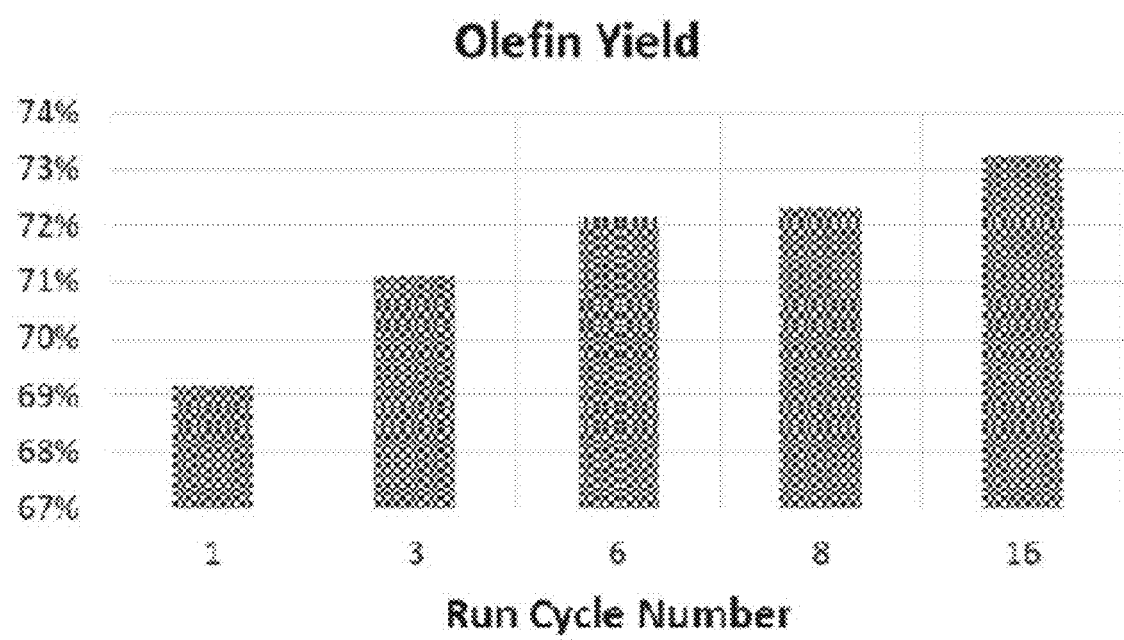
FIG. 3 shows the results of Example 1 and charts the effect of $SO_3$ injections during the purge cycle as a function of the number of $SO_3$ injections versus the yield of olefin product.

An OTA was prepared by dry mixing 10 g of $MnO_2$, 12.98 g of MgO, 3.55 g of $H_3BO_3$ and 7.64 g of $Na_4P_2O_7$. Sufficient distilled water was added to the mixture in order to form a wet paste. This paste was ball milled for 3 hours, dried at 110° C. overnight and then calcined in air at 950° C. for 16 hours. The resultant hard material was broken down and sieved to 14-30 mesh. A ½-inch ID alumina tube was charged with 5 ml of OTA and ODH runs were made using ethane as feed at 2,400 $hr^{-1}$ GHSV and 840° C. Product was collected in a gas bag for the first 15 seconds of the run and analyzed by GC. The reactor was then purged with a nitrogen flow, oxidized by air for 10 minutes at 840° C., purged with nitrogen. The results from this experiment are shown in Table 1 (cycle number 1). The selectivity to ethylene and other olefin products was 81.16% and the combined selectivity to $CO_2$ and CO was 12.36%. After cycle 1, the reactor was cooled and repacked to contain a 5 g amount of $NaHSO_4$ up-stream from the OTA bed. This portion of the reactor was maintained at about 550° C. upon reheating under a flow of nitrogen until the OTA portion of the reactor bed reached 840° C. $NaHSO_4$ is known to decompose to $SO_3$ under at 550° C. (De Vries, J. Inorg. Nucl. Chem. 31, 1307-1313 (1969)). Control experiments were performed with $NaHSO_4$ under a nitrogen flow at 550° C. that confirmed the formation of sulfuric acid in a water trap using bromothymol blue as an indicator. After charging the reactor with $NaHSO_4$ and making subsequent ODH runs, as above, the ODH results are seen in Table 1 (cycle numbers 3-16). As noted, the selectivity to olefins increased to 87.18% and the combined $CO_x$ selectivity declined to 5.15%. A chart of the effect of $SO_3$ injection during the purge cycle as a function of the number of $SO_3$ injections versus olefin yield is shown in FIG. 3. This experiment demonstrates that injection of a sulfur-containing compound, in this case $SO_3$, during the purge cycle can dramatically improve the observed selectivity of the OTA to obtain the desired olefin products in high yields.

TABLE 1

Effect of $SO_3$ Treatment of Catalyst on ODH Results

| Cycle Number | | No $SO_3$ 1 | $SO_3$ Injection in $N_2$ Purge | | | |
|---|---|---|---|---|---|---|
| | | | 3 | 6 | 8 | 16 |
| % Conversion | $C_2H_6$ | 85.23% | 85.66% | 85.17% | 84.47% | 83.99% |
| % Selectivity | Olefins | 81.16% | 83.02% | 84.75% | 85.59% | 87.18% |
| % Yield | Olefins | 69.17% | 71.11% | 72.18% | 72.30% | 73.22% |

TABLE 1-continued

Effect of $SO_3$ Treatment of Catalyst on ODH Results

| Cycle Number | | No $SO_3$ 1 | $SO_3$ Injection in $N_2$ Purge | | | |
|---|---|---|---|---|---|---|
| | | | 3 | 6 | 8 | 16 |
| % Selectivity | Carbon Dioxide | 10.20% | 8.38% | 6.88% | 6.33% | 4.85% |
| % Selectivity | Carbon Monoxide | 2.16% | 1.87% | 1.65% | 1.48% | 1.28% |
| % Yield | Carbon Dioxide | 8.69% | 7.17% | 5.86% | 5.35% | 4.07% |
| % Yield | Carbon Monoxide | 1.84% | 1.60% | 1.40% | 1.25% | 1.08% |
| % Selectivity | % $H_2$ Selectivity | 15.36% | 20.20% | 21.61% | 19.20% | 24.58% |
| % Selectivity | % $H_2O$ Selectivity | 84.64% | 79.80% | 78.39% | 80.80% | 75.42% |

Example 2

Figure 4:
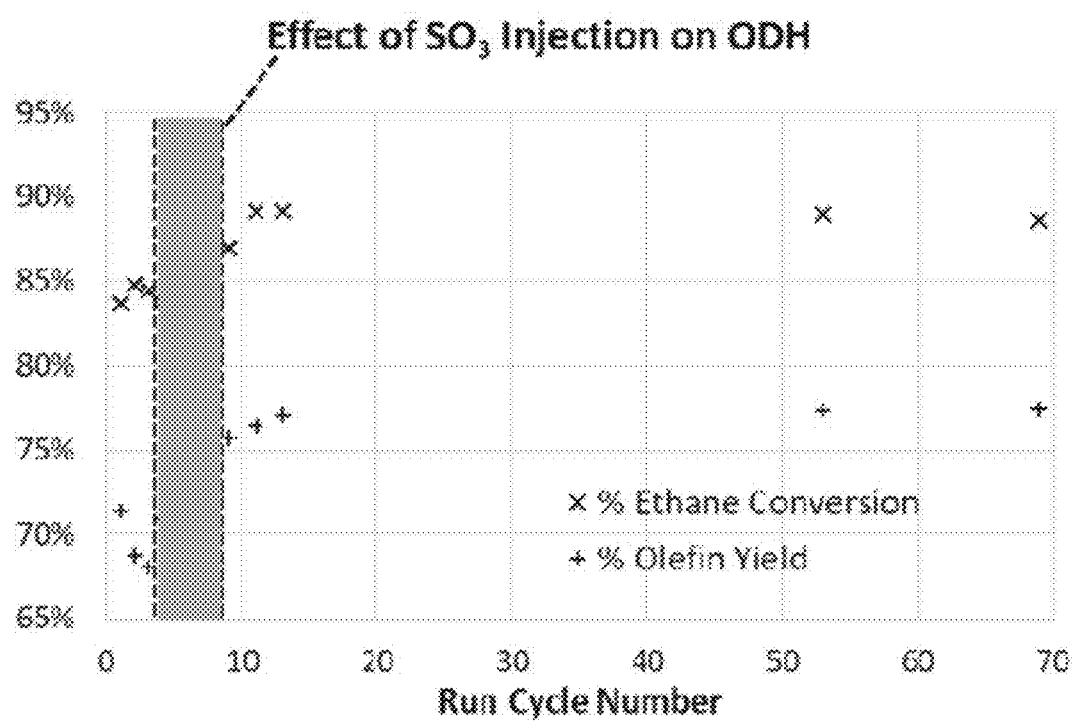
FIG. 4 shows the results of Example 2 when the described ODH reaction sequence was repeated 3 times in the absence of $SO_3$ and then run for another 66 cycles. Notably.

An OTA was prepared by dry mixing 10 g of $MnO_2$, 12.98 g of MgO, 3.55 g of $H_3BO_3$ and 1.38 g of OH. Sufficient distilled water was added to the mixture in order to form a wet paste. This paste was ball milled for 3 hours, dried at 110° C. overnight and then calcined in air at 950° C. for 16 hours. The resultant hard material was broken down and sieved to 14-30 mesh. A ½-Inch ID alumina tube was charged with 5 ml of OTA and ODH runs were made using ethane as feed at 2,400 $hr^{-1}$ GHSV and 840° C. Product was collected in a gas bag for the first 15 seconds of the run and analyzed by GC. The reactor was then purged with a nitrogen flow, oxidized by air for 10 minutes at 840° C., purged with nitrogen. This sequence was repeated 3 times and the results are shown in Table 2. The conversion for cycles 1-3 was 84-84% and the yield to ethylene and other olefin products was 68-71% as shown in FIG. 4. After cycle 3, the reactor was cooled and repacked to contain a 5 g amount of $NaHSO_4$ up-stream from the OTA bed. This portion of the reactor was maintained at about 550° C. upon reheating under a flow of nitrogen until the OTA portion of the reactor bed reach 840° C. The unit was then run for another 66 cycles. Titration of the effluent purge gas indicated that the $NaHSO_4$ was totally converted to $SO_3$ after a total of 9 cycles. The selectivity to olefin products increased to over 87% and was maintained through cycle 69. FIG. 4 shows the beneficial effects of increasing ethane conversion and olefin yield after the $SO_3$ had been injected into the nitrogen purge stream. This beneficial effect unexpectedly remained in place for approximately 60 cycles after the $SO_3$ injection had occurred.

TABLE 2

Effect of $SO_3$ Injection on ODH Results

| | | $NoSO_3$ | | | | | | $SO_3$ during $N_2$ Purge | | | | | |
|---|---|---|---|---|---|---|---|---|---|---|---|---|---|
| | | 1 | 2 | 3 | 4 | 5 | 7 | 8 | 9 | 11 | 13 | 53 | 69 |
| % Conversion | CH4/C2H6/C3H8 | 83.67% | 84.77% | 84.40% | 83.72% | 84.34% | 84.15% | 83.62% | 86.94% | 89.18% | 89.16% | 88.94% | 88.64% |
| % Selectivity | $C_2^+$ | 85.38% | 81.05% | 80.58% | 84.62% | 84.79% | 86.01% | 86.58% | 87.16% | 85.73% | 86.42% | 86.94% | 87.39% |
| % Yield | $C_2^+$ | 71.43% | 68.70% | 68.02% | 70.84% | 71.52% | 72.38% | 72.40% | 75.78% | 76.45% | 77.05% | 77.33% | 77.46% |
| | Carbon Dioxide | 4.93% | 9.53% | 9.86% | 5.79% | 5.47% | 4.44% | 4.03% | 2.50% | 3.08% | 2.63% | 2.86% | 1.97% |

TABLE 2-continued

Effect of SO₃ Injection on ODH Results

| | | NoSO₁ | | | | | | SO₂ during N₂ Purge | | | | | |
|---|---|---|---|---|---|---|---|---|---|---|---|---|---|
| | | 1 | 2 | 3 | 4 | 5 | 7 | 8 | 9 | 11 | 13 | 53 | 69 |
| % Selectivity | Carbon Monoxide | 1.80% | 2.34% | 2.38% | 2.13% | 2.14% | 1.92% | 1.80% | 1.74% | 2.56% | 2.40% | 1.41% | 1.29% |
| | Carbon Dioxide | 4.12% | 8.08% | 8.33% | 4.85% | 4.61% | 3.74% | 3.37% | 2.17% | 2.75% | 2.35% | 2.54% | 1.75% |
| % Yield | Carbon Monoxide | 1.50% | 1.98% | 2.01% | 1.79% | 1.81% | 1.62% | 1.51% | 1.52% | 2.28% | 2.14% | 1.26% | 1.14% |
| | %H2 Selectivity | 30.92% | 29.30% | 29.21% | 19.36% | 19.59% | 20.44% | 20.67% | 26.91% | 27.85% | 27.59% | 29.32% | 36.59% |
| % Selectivity | %H2O Selectivity | 69.08% | 70.70% | 70.79% | 80.64% | 80.41% | 79.56% | 79.33% | 73.09% | 72.15% | 72.41% | 70.68% | 63.41% |

Example 3

Figure 5:
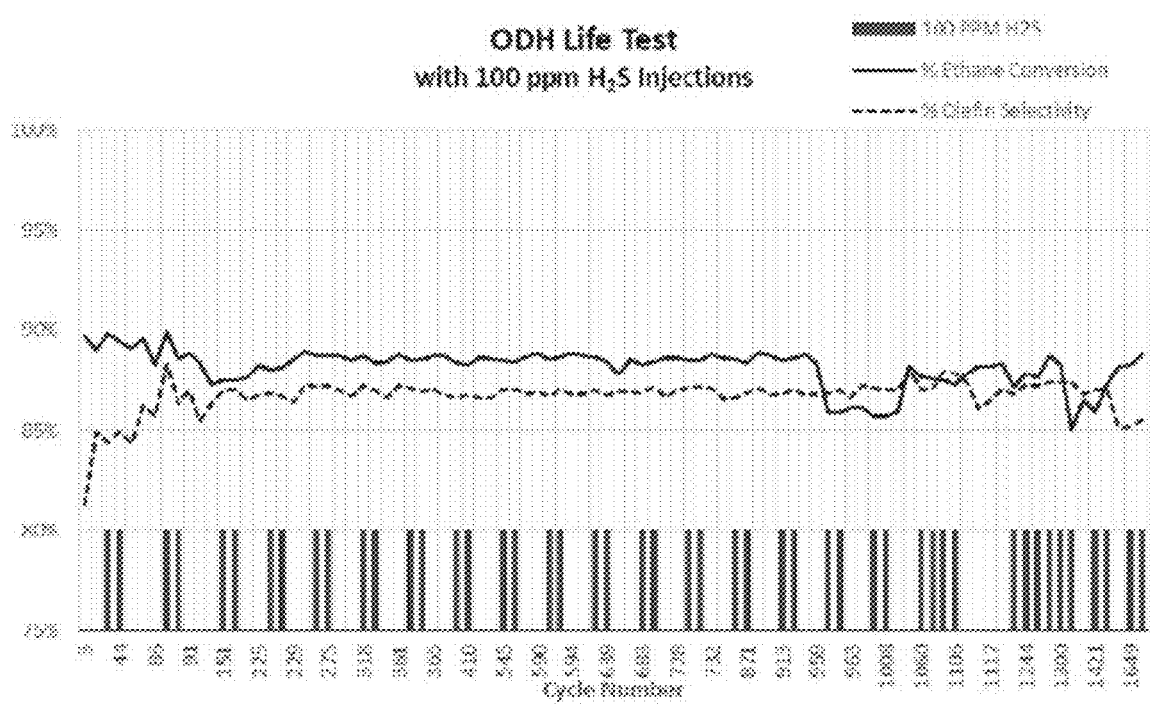
FIG. 5 summarizes the results of Example 3 and shows that intermittent substitution of 100 ppm of $H_2S$ in nitrogen for pure nitrogen in a reactor purge step over 1,649 reaction cycles surprisingly led to a significant benefit to the ODH olefin selectivity with no detrimental effect on the OTA conversion rate.

An OTA was prepared by dry mixing 12.88 g of MnO₂, 16.92 g of MgO, 4.52 g of H₃BO₃, 14.81 g of Na₄P₂O₇, 2.58 g of ammonium metatungstate hydrate and 8.58 g of Ludox AS30. Sufficient distilled water was added to the mixture in order to form a wet paste which was spray dried to form spheres of 70 micron average particle size. The spray dried material was then calcined air at 950° C. for 16 hours. A 3-Inch ID alumina tube was charged with 5 ml of spay dried OTA and ODH fluid bed runs were made using ethane as feed at 2,400 hr⁻¹ GHSV and 840° C. Product was collected in a gas bag for the first 15 seconds of the run and analyzed by GC. The reactor was then purged with a nitrogen flow, oxidized by air for 10 minutes at 840° C., purged with nitrogen. This sequence was repeated 1,649 times with over one month of on-stream time. The results are summarized in FIG. 5. During this experiment, 100 ppm H₂S in nitrogen was intermittently substituted for pure nitrogen. Over the first 86 cycles the olefin selective increased from 81% to 87% and was maintained for the period of the experiment. Surprisingly, and in contrast to conventional reports about catalysis, the presence of H₂S in the purge stream conferred a significant benefit to the ODH olefin selectivity and did not have a detrimental effect of OTA conversion rate.

Example 4

An OTA was prepared by dry mixing 10 g of MnO₂, 12.98 g of MgO, 3.55 g of H₃BO₃ and 1.38 g of OH. Sufficient distilled water was added to the mixture in order to form a wet paste. This paste was ball milled for 3 hours, dried at 110° C. overnight and then calcined in air at 950° C. for 16 hours. The density of this OTA was 0.8 g/cc. The resultant hard material was broken down and sieved to 14-30 mesh. A ½-inch ID alumina tube was charged with 5 ml of OTA and ODH runs were made using ethane as feed at 2,400 hr⁻¹ GHSV and 840° C. Product was collected in a gas bag for the first 15 seconds of the run and analyzed by GC. The reactor was then purged with a nitrogen flow, oxidized by air for 10 minutes at 840° C., purged with nitrogen. Ethane conversion for was 82-84% and the yield to ethylene and other olefin products was 68-71%.

Example 5

An OTA was prepared by dry mixing 10 g of MnO₂, 12.98 g of MgO, 3.55 g of H₃BO₃ and 1.38 g of LiOH. Sufficient distilled water was added to the mixture in order to form a wet paste. This paste was ball milled for 3 hours, dried at 110° C. overnight. The OTA was then treated in a flow of 4% hydrogen in nitrogen at 950° C. in a sealed rotary calciner. Sufficient hydrogen flow was provided to supply 1.5 stoichiometric equivalents of hydrogen reducing agent compared to the moles of manganese present, assuming the manganese was in the +4 oxidation state. This reduced material was then calcined in air at 950° C. for 16 hours. The density of this OTA was 1.4 g/cc. The resultant hard material was broken down and sieved to 14-30 mesh. A ½-inch ID alumina tube was charged with 5 ml of OTA and ODH runs were conducted using ethane as a feed at 2,400 hr⁻¹ GHSV and 840° C. Product was collected in a gas bag for the first 15 seconds of the run and analyzed by GC. The reactor was then purged with a nitrogen flow, oxidized by air for 10 minutes at 840° C., purged with nitrogen. Ethane conversion for was 80-83% and the yield to ethylene and other olefin products was 68-71%.

Example 6

An OTA was prepared by dry mixing 10 g of MnO₂, 12.98 g of MgO, 3.55 g of H₃BO₃ and 1.38 g of OH. Sufficient distilled water was added to the mixture in order to form a wet paste. This paste was ball milled for 3 hours, dried at 110° C. overnight. The OTA was then mixed with sufficient activated carbon to, under the presence of steam, produce 2 equivalents of hydrogen based on the manganese present (assuming the manganese was in a +4 oxidation state). The mixture was placed in a fluidized bed and treated with steam at 900° C. for two hours. This reduced material was then calcined in air at 950° C. for 16 hours. The density of this OTA was 1.45 g/cc. The resultant hard material was run for ODH in a fluidized bed after sieving to an average particle size of 70 microns. A h-inch ID alumina tube was charged with 5 ml of OTA and ODH runs were made using an up-flow ethane as feed at 2,400 hr⁻¹ GHSV and 840° C. Product was collected in a gas bag for the first 15 seconds of the run and analyzed by GC. The reactor was then purged with a nitrogen flow, oxidized by air for 10 minutes at 840° C., purged with nitrogen. Ethane conversion for was 83-85% and the yield to ethylene and other olefin products was 66-71%.

Example 7

Figure 6:
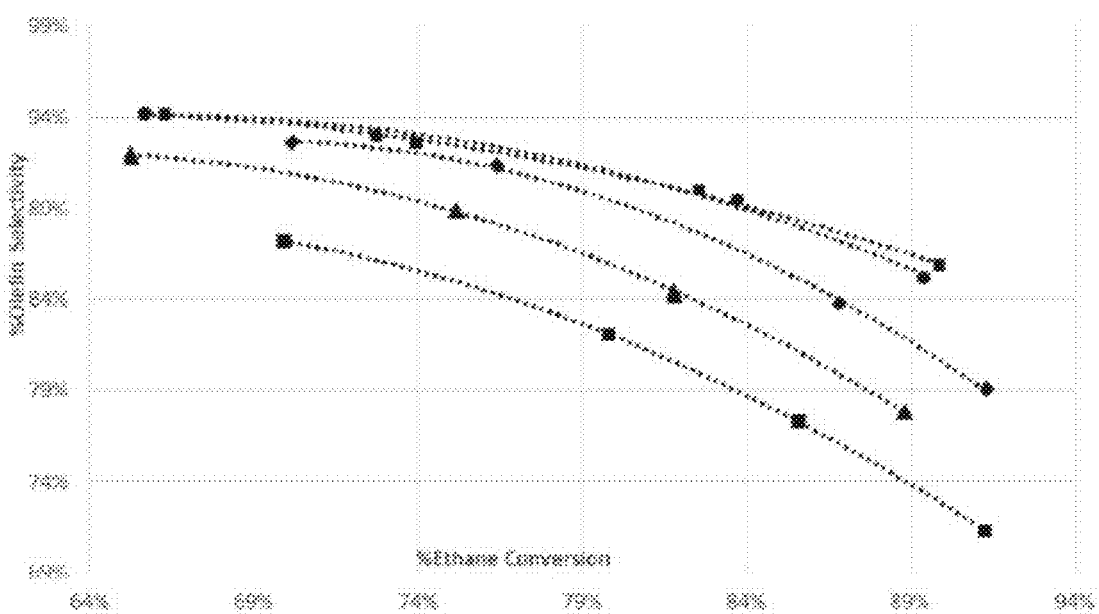
FIG. 6 shows the ethane conversion and olefin selectivity results of several ODH reaction cycles as described in Example 4 where the OTA in the hydrocarbon conversion reactor is subjected to air oxidation for 10 minutes at 840° C. as part of the purging sequence.

An OTA was prepared by dry mixing 10 g of MnO₂, 12.98 g of MgO, 3.55 g of H₃BO₃, 1.38 g of LiOH and 9.91 g of CaSO₄. Sufficient distilled water was added to the mixture in order to form a wet paste. This paste was ball milled for 3 hours, dried at 110° C. overnight and then calcined in air at 950° C. for 16 hours. The resultant hard material was broken down and sieved to 14-30 mesh. A h-inch ID alumina tube was charged with 5 ml of OTA and ODH runs were made using ethane as feed at 2,400 hr⁻¹ GHSV and 840° C. Product was collected in a gas bag for the first 15 seconds of the run and analyzed by GC. The reactor was then purged with a nitrogen flow, oxidized by air for 10 minutes at 840° C., purged with nitrogen. This sequence was then repeated many times. A representative run result is shown in Table 3. The conversion and selectivities for these runs is shown as the top curve in FIG. 6. This result by the OTA was compared to similar conditions with other ODH OTAs known in the literature (see, e.g., U.S. Pat. Nos. 4,777,313; and 10,138,182). In all examples, the selectivity to the desired olefinic products is much lower at the beginning of the run, when the first amount of oxygen is removed from the OTA and the ethane conversion is in the range of 88-94%. As the active oxygen from the OTA is removed, the ODH selectivity increases.

TABLE 3

Ethane to Olefin ODH Results

| % Conversion | $C_2H_6$ | 89.87% |
|---|---|---|
| % Selectivity | Olefins | 83.31% |
| % Yield | Olefins | 81.76% |
| % Selectivity | Carbon Dioxide | 3.63% |
| % Selectivity | Carbon Monoxide | 2.17% |
| % Yield | Carbon Dioxide | 3.26% |
| % Yield | Carbon Monoxide | 1.95% |
| % Selectivity | % $H_2$ Selectivity | 26.43% |
| % Selectivity | % $H_2O$ Selectivity | 73.57% |

Figure 7:
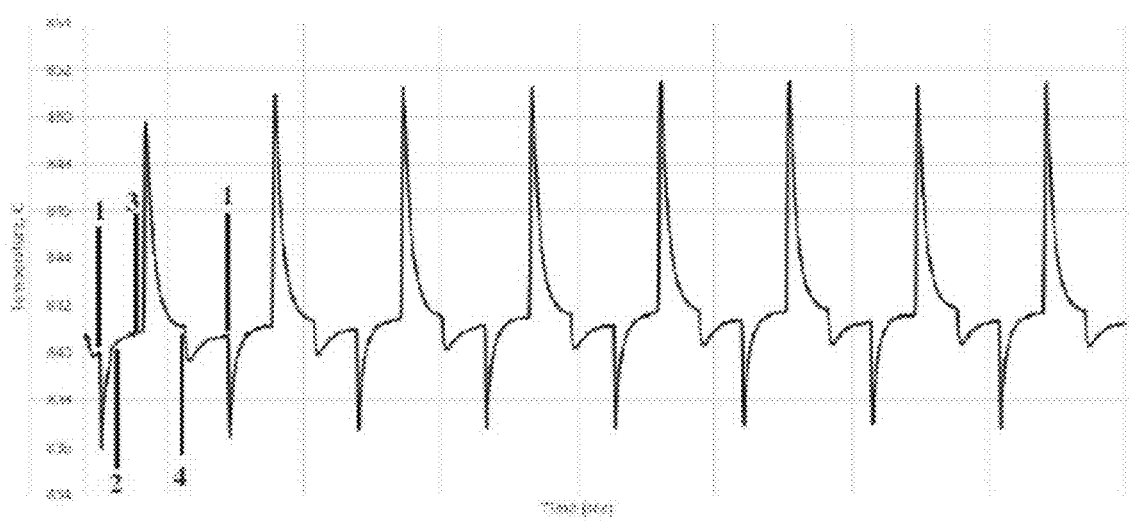
FIG. 7 shows the heat profile results of placing a thermocouple in the middle of the OTA bed of Example 4, where the reaction sequence is started at 1 where nitrogen is flushed from the system by the introduction of ethane. A decrease in reactor temperature indicates that an endothermic reaction 2 is proceeding. At 2, nitrogen is introduced to the reactor to remove all products and the ethane feed. At 3, air is introduced and a large exotherm is observed which is the result of the re-oxidation of the reduced OTA to its oxidized form. Nitrogen is re-introduced at 4.
Figure 8:
FIG. 8 shows the pyrolysis of ethane under identical conditions to that shown in FIG. 7 but with the replacement of the OTA by dense α-alumina. The introduction of ethane at 1 resulted in a larger temperature decline due to the reaction being the purely endothermic conversion of ethane to olefins and hydrogen. When air is introduced at 3, only a small exotherm resulted due to the burning off of coke.

A thermocouple placed in the middle of the OTA bed of Example 7 is shown in FIG. 7 which shows the heat profile of the described sequence over multiple cycles. The reaction sequence was started at 1 where nitrogen was flushed from the system by the introduction of ethane. A decrease in reactor temperature indicates that an endothermic reaction 2 was proceeding. The OTA in this cycle converted 73.57% of the hydrogen to water. FIG. 8 shows the pyrolysis of ethane under identical conditions except that the OTA was replaced with dense α-alumina. As seen in FIG. 8, the introduction of ethane at 1 resulted in a much larger temperature decline (by comparison to FIG. 7) because the reaction was purely the endothermic conversion of ethane to olefins and hydrogen. To continue with the explanation of FIG. 7, at 2 nitrogen was introduced to the reactor to remove all products and the ethane feed. At 3, air was introduced and a large exotherm was observed, which is the result of the re-oxidation of the reduced OTA to its oxidized form, i.e., the reverse of reaction (2). By comparison, the α-alumina reactor depicted in FIG. 3 showed only a small exotherm as a result of burning off coke. In FIG. 7, after the re-oxidation was completed, nitrogen was re-introduced at 4. Surprisingly, a drop in reactor temperature was observed indicating an endothermic loss of NSRO from the OTA. It was observed that the removal of the NSRO in this purge after the OTA re-oxidation lead to more selective ODH and OCM results. Therefore, the purge step of 4 was sufficient in time and the volume of purge gas such that most of the NSRO was removed from the OTA.

The ODH and OCM reactions can be accomplished in any reactor type that operates continuously or step-wise via a fixed bed reactor, which switches the reactor environment of the OTA from a reducing hydrocarbon environment to an oxidizing environment. In an exemplary embodiment, a key feature of the technique to remove NSRO from OTAs before use of the OTA in an ODH reaction of hydrocarbons is to employ only a portion of the purge or stripping cycle to remove NSRO from the OTA. The OCM and ODH reactions may also be carried out in reactors whereby the hydrocarbon and an oxidizing gas, such as oxygen or air, is used to catalytically promote equation 3. In this embodiment, the selectivity of the catalytic reaction is improved by pre-treating the OTA as described herein before the OTA is charged to the reactor. In addition, running a catalytic OCM or ODH reactor with oxygen feeds that are below the stoichometric reaction requirement, and thus providing a steady state OTA that is partially reduced, should also have a positive effect on improving the desired product selectivities.

DISCUSSION

Examples 1 to 3 demonstrate that sulfur-containing compounds such as a $SO_3$ and $H_2S$ that comprise a portion of the purge gas can significantly increase the selectivity of OTAs and maintain this benefit for many cycles. This beneficial effect is not limited to $SO_3$ and $H_2S$ and should be present when employing any form of sulfur, such as, but not limited to, elemental sulfur vapor, $SO_2$, $CS_2$, organo-sulfur compounds and any other commonly available forms of sulfur that can be readily converted to a gaseous state.

While Examples 1 to 3 were run at a reaction temperature of 840° C., this temperature is only exemplary and the application of this invention is not constrained by the temperature at which the sulfur-containing compound is exposed to the catalyst or OTA. Treatment of the catalyst or OTA pre-cursors with a sulfur-containing compound at a temperature range of, for example, 1° C. to 1,100° C. Is sufficient to condition and improve the catalyst or OTA as long as the conditions allow for interaction (such as adsorption) of the sulfur moiety of the sulfur-containing compound with the precursors.

In an exemplary embodiment, the conditioning of the catalyst, the OTA and the catalyst/OTA precursor materials is accomplished via liquid phase impregnation of these materials. In this case, in addition to the sulfur-containing compounds described herein, liquid impregnation with any of these compounds (including, but not limited to, sulfuric acid, sulfurous acid and salts thereof) will result in the same beneficial conditioning of the catalysts and OTAs and their use for OCM and ODH reactions.

In addition to the OCM and ODH reactor systems described herein in which OTAs are used in a redox cyclic mode, the present invention may also be applied to improve the stability and product yields for catalytic OCM and ODH reactions which are run by co-feeding a hydrocarbon and an oxygen-containing gas to a reactor. A key distinguishing feature of the present invention is to perform the catalyst or OTA conditioning at a site that is separate from the reactor vessel and/or in a separate step apart from the catalytic hydrocarbon conversion. By following this practice, possible corrosion of the reactor components due to the presence of sulfur-containing gases and the possible formation of undesired organo-sulfur by-products are avoided. As with the redox system, catalyst and OTA conditioning may be conducted in a continuous process that is intimately linked to the OCM or ODH process or alternatively, in batch processes that are discounted from and not limited to either the process or the location of the OCM or ODH reactor systems.

Examples 4 to 6 exemplify densification of the OTA which improves the fluid bed attrition resistance of the OTA particles and also allows for higher oxygen transport rates and improved heat transfer between reaction vessels in which the OTA is transported.

In Examples 4 to 6, the densification of the OTA can be carried out at the catalyst manufacturing site or at the ODH reaction site using dedicated equipment. The examples are not intended to be limiting, however, and the catalyst and/or OTA can also be subject to continuous densification of the catalyst/OTA as shown in FIG. 2.

Example 7 exemplifies removal of NSRA from OTAs and the resulting in improved selectivity for the desired olefinic product. While nitrogen was used to illustrate the reducing gas in Example 7, any gas that affects the removal of NSRO from the OTA before the OTA is used to promote equation (3) is considered suitable, and may include, but is not limited to, steam, Group 18 inert gases, methane, oxides of carbon, oxides of nitrogen, oxides of sulfur, sulfur-containing compounds that do not react with the OTA or in general, and gaseous streams that can extract NSRO from the OTA but not be oxidized by the OTA during this removal process. Although the removal of interstitial or physisorbed oxygen present in, for example, circulating bed reactors, is not a particular objective of the present invention, such interstitial and physisorbed oxygen may also be removed in whole or in part during the process described herein for removing NSRO from the OTA.

In general, the teachings of the present invention may be applied to improve the lifetime of the catalyst and/or OTA and to achieve selectivities to the desired products utilizing any catalyst or OTA that contains alkali metal or alkaline earth promoters.

Within this specification, embodiments have been described in a way which enables a clear and concise specification to be written, but it is intended and will be appreciated that the embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the invention. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A process for enhancing at least one of selectivity, rate and yield associated with using an oxygen transfer agent for oxidative dehydrogenation of a saturated hydrocarbon, the process comprising:
   treating the oxygen transfer agent with a sulfur-containing compound at a site or at a time that is different from where and when the saturated hydrocarbon is converted by the oxygen transfer agent to an unsaturated hydrocarbon, and then
   reacting the treated oxygen transfer agent with the saturated hydrocarbon to produce the unsaturated hydrocarbon and water, where the treated oxygen transfer agent supplies oxygen required for oxidative dehydrogenation of the saturated hydrocarbon and for formation of the water and is reduced in the process,
   wherein the treatment of the oxygen transfer agent with the sulfur-containing compound reduces carbon oxide ($CO_x$) formation during reaction of the treated oxygen transfer agent with the saturated hydrocarbon.

2. The process according to claim 1, wherein the site is a conditioning vessel where unconditioned oxygen transfer agent is conditioned.

3. The process according to claim 1, wherein the site is a standpipe or a gas stripper section in a circulation bed reactor.

4. The process according to claim 1, wherein the site is a location at a facility where the unsaturated hydrocarbon is produced.

5. The process according to claim 1, wherein the sulfur-containing compound is a liquid or a gas.

6. The process according to claim 1, wherein the sulfur-containing compound is selected from the group consisting of dimethyl sulfide, diethyl sulfide, ethylene sulfide, diamyl sulfide, diallyl sulfide, dicyclohexyl sulfide, $H_2S$ and $CS_2$.

7. The process according to claim 1, wherein the saturated hydrocarbon is a $C_2$-$C_6$ saturated hydrocarbon.

8. The process according to claim 1, wherein the saturated hydrocarbon is ethane or propane.

9. The process according to claim 1, wherein the saturated hydrocarbon is ethane, where the ethane is generated by oxidative coupling of methane.

10. The process according to claim 1, further comprising increasing particle density of the oxygen transfer agent to enhance attrition resistance of the particles by treating the oxygen transfer agent with a reducing agent at a site different from where the saturated hydrocarbon is converted by the oxygen transfer agent to the unsaturated hydrocarbon.

11. The process according to claim 10, wherein treatment of the oxygen transfer agent with the reducing agent occurs before treatment of the oxygen transfer agent with the sulfur-containing compound.

12. The process according to claim 10, wherein treatment of the oxygen transfer agent with the reducing agent occurs after treatment of the oxygen transfer agent with the sulfur-containing compound.

13. The process according to claim 10, wherein the reducing agent is hydrogen gas, nitrous oxide or carbon monoxide.

14. The process according to claim 13, wherein the hydrogen gas and carbon monoxide are generated at the site where the saturated hydrocarbon is converted by the oxygen transfer agent to the unsaturated hydrocarbon.

15. The process according to claim 14, wherein the hydrogen gas and/or the carbon monoxide are by-products formed from the oxidative dehydrogenation of the saturated hydrocarbon to the unsaturated hydrocarbon.

16. The process according to claim 14, wherein the reducing agent is generated from combustion of carbonaceous materials.

17. The process according to claim 10, wherein the particle density is increased by at least 10%.

18. The process according to claim 10, wherein the particle density is increased by at least 20%.

19. The process according to claim 10, wherein the particle density is increased by at least 30%.

20. The process according to claim 1, further comprising increasing the selectivity of the oxygen transfer agent for oxidative dehydrogenation of a saturated hydrocarbon by removing non-selective redox oxygen (NSRO) present on the oxygen transfer agent by subjecting the oxygen transfer agent to a gas that is substantially free of any molecular oxygen.

21. The process according to claim 20, wherein subjecting the oxygen transfer agent to the gas partially reduces the oxygen transfer agent.

22. The process according to claim 20, wherein the gas is nitrogen gas, argon, methane, oxides of carbon, oxides of nitrogen or oxides of sulfur.

23. The process according to claim 20, wherein the selectivity is increased by at least 5%.

24. The process according to claim 20, wherein the selectivity is increased by at least 10%.

25. The process according to claim 20, wherein the selectivity is increased by at least 20%.

26. The process according to claim 1, wherein the sulfur-containing compound is an oxide of sulfur and where the oxide of sulfur also supplies oxygen required for oxidative dehydrogenation of the saturated hydrocarbon and for formation of the water.

27. The process according to claim 26, wherein the oxide of sulfur is $SO_3$ or $SO_2$.

28. A process for reducing corrosion of reactor components in a reactor where a saturated hydrocarbon is converted by an oxygen transfer agent to an unsaturated hydrocarbon, the process comprising:

treating the oxygen transfer agent at a site that is different from the reactor with a sulfur-containing compound that enhances at least one of selectivity, rate and yield associated with using the oxygen transfer agent, and reacting the treated oxygen transfer agent with the saturated hydrocarbon to produce the unsaturated hydrocarbon and water, where the treated oxygen transfer agent supplies oxygen required for conversion of the saturated hydrocarbon to the unsaturated hydrocarbon and for formation of the water and is reduced in the process, wherein the treatment of the oxygen transfer agent with the sulfur-containing compound reduces carbon oxide (COx) formation during reaction of the treated oxygen transfer agent with the saturated hydrocarbon.

29. The process according to claim 28, wherein the sulfur-containing compound is an oxide of sulfur and where the oxide of sulfur also supplies oxygen required for oxidative dehydrogenation of the saturated hydrocarbon and for formation of the water.

30. The process according to claim 29, wherein the oxide of sulfur is $SO_3$ or $SO_2$.

* * * * *